(12) United States Patent
Hsueh et al.

(10) Patent No.: US 11,324,171 B2
(45) Date of Patent: May 10, 2022

(54) SMART PLANT GROWTH SYSTEM

(71) Applicant: Aessense Technology Hong Kong Limited, Harbour (CN)

(72) Inventors: Wenpeng Hsueh, San Ramon, CA (US); Shengyang Wang, Shanghai (CN); Hairong Lv, Shanghai (CN); Chao-Hsien Wu, Shanghai (CN)

(73) Assignee: Aessense Technology Hong Kong utd., Hong Kong (HK)

( * ) Notice: Subject to any disclaimer, the term of this patent is extended or adjusted under 35 U.S.C. 154(b) by 342 days.

(21) Appl. No.: 16/277,675

(22) Filed: Feb. 15, 2019

(65) Prior Publication Data
US 2019/0246559 A1 Aug. 15, 2019

Related U.S. Application Data

(60) Provisional application No. 62/631,041, filed on Feb. 15, 2018.

(51) Int. Cl.
| | | |
|---|---|---|
| A01G 25/16 | (2006.01) | |
| G01N 33/18 | (2006.01) | |
| G01N 33/00 | (2006.01) | |
| A01G 31/02 | (2006.01) | |
| A01G 31/06 | (2006.01) | |
| A01C 23/00 | (2006.01) | |
| A01C 23/04 | (2006.01) | |

(Continued)

(52) U.S. Cl.
CPC ............ *A01G 25/16* (2013.01); *A01C 23/007* (2013.01); *A01C 23/047* (2013.01); *A01G 9/023* (2013.01); *A01G 27/001* (2013.01); *A01G 27/003* (2013.01); *A01G 27/008* (2013.01); *A01G 27/02* (2013.01); *A01G 31/02* (2013.01); *A01G 31/06* (2013.01); *G01N 33/0098* (2013.01); *G01N 33/18* (2013.01); *H04L 67/125* (2013.01); *A01G 2/10* (2018.02)

(58) Field of Classification Search
CPC ........ A01G 25/16; A01G 31/02; A01G 31/06; A01G 9/023; A01G 27/001; A01G 27/003; A01G 27/02; A01G 27/008
See application file for complete search history.

(56) References Cited

U.S. PATENT DOCUMENTS 9,668,434 B2 6/2017 Kernahan
9,693,512 B2 7/2017 Chen et al.
(Continued)

FOREIGN PATENT DOCUMENTS

DE 102018101697 B3 * 4/2019 ............... C02F 1/325
DE 102018114954 A1 * 12/2019 ........... G06K 19/045
(Continued)

*Primary Examiner* — Monica L Barlow
*Assistant Examiner* — Aaron M Rodziwicz
(74) *Attorney, Agent, or Firm* — David Millers

(57) ABSTRACT

An aeroponic plant-growth system includes growth space and a control unit that may be assembled using factory made modules. The growth space includes layers at different heights, and each layer includes plant holders and misters positioned to apply a mist to roots of plants in the plant holders. The control unit employs a controller to execute a program that operates a liquid supply system to provide liquid flows to the misters in the layers. Each of the liquid flows may be regulated according to the height of the layers.

17 Claims, 4 Drawing Sheets

(51) Int. Cl.
  *A01G 9/02*   (2018.01)
  *A01G 27/00*  (2006.01)
  *A01G 27/02*  (2006.01)
  *H04L 67/125* (2022.01)
  *A01G 2/10*       (2018.01)

(56) References Cited

U.S. PATENT DOCUMENTS

| | | | |
|---|---|---|---|
| 10,477,786 B1* | 11/2019 | Wilson | A01G 31/047 |
| 2016/0021836 A1 | 1/2016 | Kernahan | |
| 2016/0021837 A1 | 1/2016 | Kernahan | |
| 2016/0028442 A1 | 1/2016 | Kernahan | |
| 2016/0128289 A1 | 5/2016 | Wong et al. | |
| 2016/0242372 A1 | 8/2016 | Wong et al. | |
| 2016/0255781 A1 | 9/2016 | Chen et al. | |
| 2017/0094920 A1* | 4/2017 | Ellins | A01G 31/02 |
| 2018/0308028 A1 | 10/2018 | Zhang et al. | |
| 2018/0325038 A1* | 11/2018 | Spiro | A01G 27/001 |
| 2019/0021249 A1* | 1/2019 | Ivanescu | A01G 9/047 |
| 2019/0183062 A1* | 6/2019 | Pham | A01G 31/06 |
| 2019/0191643 A1* | 6/2019 | Chan | A01G 27/001 |
| 2019/0208711 A1* | 7/2019 | Sahu | A01G 31/06 |
| 2019/0261589 A1* | 8/2019 | Pham | A01G 9/0297 |
| 2020/0260653 A1* | 8/2020 | Douglas | A01G 27/003 |
| 2020/0375120 A1* | 12/2020 | Kaneko | A01G 9/023 |
| 2021/0007307 A1* | 1/2021 | Adams | A01G 27/06 |

FOREIGN PATENT DOCUMENTS

| | | | | |
|---|---|---|---|---|
| DE | 102018007342 A1 * | 3/2020 | | A01G 27/02 |
| DE | 102018129987 A1 * | 5/2020 | | A01G 9/025 |
| EP | 3695710 A1 * | 8/2020 | | A01G 9/0295 |
| FR | 2511842 A1 * | 3/1983 | | A01G 27/001 |
| WO | 2016014865 A1 | 1/2016 | | |
| WO | 2016018767 A1 | 2/2016 | | |
| WO | WO-2019030428 A1 * | 2/2019 | | A01G 31/042 |
| WO | WO-2019051261 A1 * | 3/2019 | | A01G 27/001 |
| WO | WO-2020057828 A1 * | 3/2020 | | A01G 31/06 |

* cited by examiner

SMART PLANT GROWTH SYSTEM

CROSS-REFERENCE TO RELATED APPLICATIONS

This patent document claims benefit of the earlier filing date of U.S. provisional Pat. App. No. 62/631,041, filed Feb. 15, 2018, which is hereby incorporated by reference in its entirety.

BACKGROUND

Indoor systems have been developed for growing plants. For example, hydroponic systems can grow plants without soil, e.g., with roots suspended in air, liquid or other media and plant nutrients provided in an aqueous solution that may be applied to the roots. A hydroponic system that employs aeroponic techniques, e.g., with plant roots predominantly suspended in the air and nutrient solution delivered to the roots in a mist, is described in U.S. Pat. App. Pub. No. 2016/0021836, entitled "Aeroponic Growth System Wireless Control System and Methods of Using," published Jan. 28, 2016, which is hereby incorporated by reference in its entirety. Such indoor plant growth systems may be assembled using factory-made modules, with each module being capable of growing a plant, a few plants, or a few dozen plants.

A commercial indoor plant growth facility would typically require many plant growth modules arranged within the available space in a building. The modules need to be connected to infrastructure of the building such as a water supply, drain pipes, and electrical power, and control and/or monitoring systems may also need to be connected to the modules and to the available infrastructure. Even with the currently available plant growth modules that may integrate many systems for satisfying plant growth needs, setting up and operating a large scale plant growth facility that efficiently uses available indoor space and infrastructure and that promotes high crop production and plant growth can be a complex task.

BRIEF DESCRIPTION OF THE DRAWINGS

The drawings illustrate examples for the purpose of explanation and are not of the invention itself. Use of the same reference symbols in different figures indicates similar or identical items.

DETAILED DESCRIPTION

In accordance with one aspect disclosed herein, a plant growth system may includes modules that provide multiple stacked levels for growing plants. Each level may include one or more drawers that may be slid out for horticultural operations such as planting, repotting, or harvesting of plants or maintenance operations such as cleaning, maintenance, or repairs. The drawers may be vertically stacked to improve yield per available floor space at a plant growing facility. Growth space modules including the stacks of drawers may further be organized into rows that may share resources such as a control module including a row controller, a dosing system, and a liquid supply system. Each row may be logically split into layers, each layer corresponding to blocks of drawers at substantially the same height in different plant-growth modules. Operations such as supply of water or nutrient solution to plants may be performed on individual levels. Further, a multi-row bank of modules may include space for an aisle between two of the rows in the bank, and each row of modules may be mobile as a unit. The location of the aisle may be changed by moving a row of modules next to the aisle into the space formerly used for the aisle, so that a new aisle opens up on an opposite side of the moved row.

A plant growth system in accordance with one implementation of the invention includes two main portions, a growth space (GS) and a control unit (CU). The growth space includes structures for holding and growing plants and includes devices for providing for the needs of the plants, e.g., lights, ventilation systems, and nutrient applicators. The growth space may also include sensors for monitoring the plants and/or the other devices in the growth space. The growth space may be provided, constructed, or assembled using one or more "growth space modules." The control unit, which may be a distributed or centralized system, controls and monitors all devices in the system and may be provided, constructed, or assembled using one or more "control unit modules."

Figure 1A:
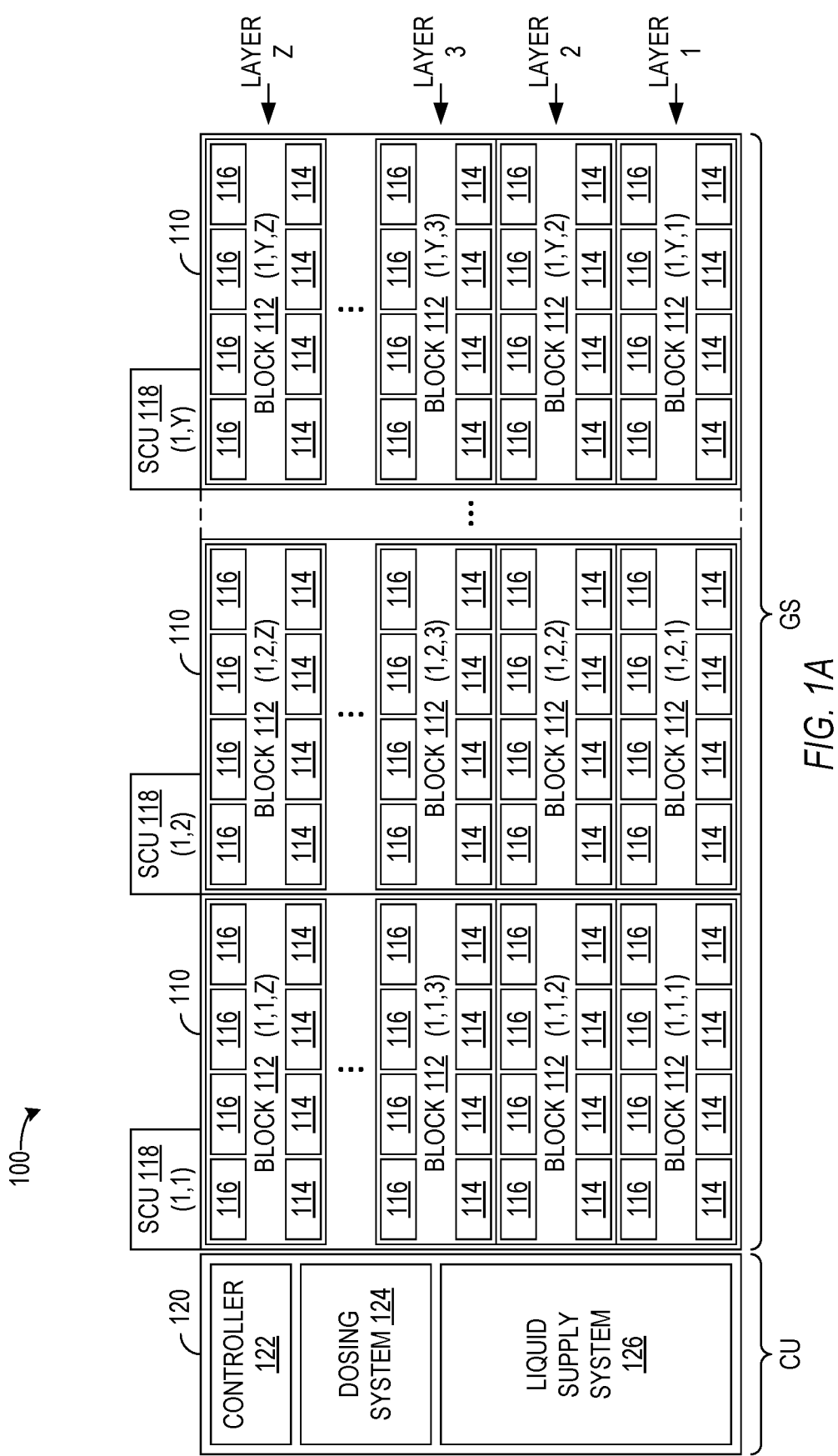
FIG. 1A is a block diagram illustrating a side view of a plant growth system having a row that includes a control unit module and multi-layer, growth space modules.
Figure 1B:
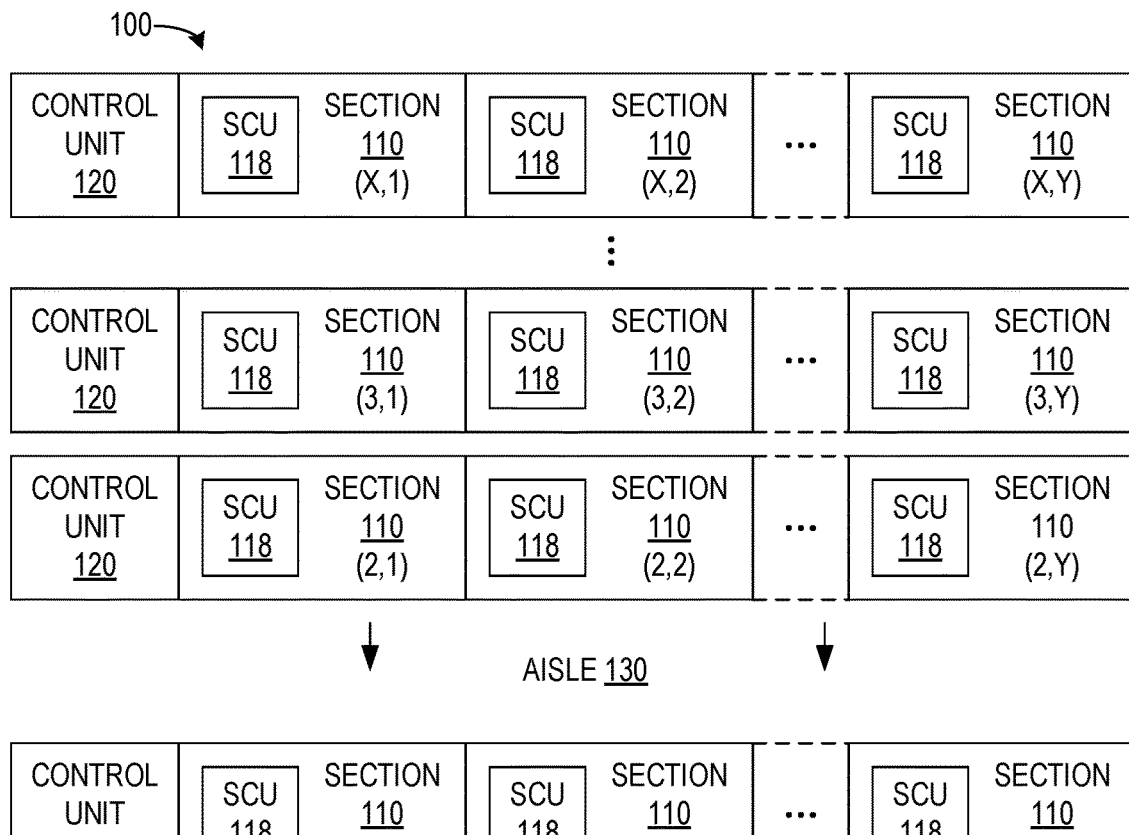
FIGS. 1B and 1C are block diagrams illustrating top views of a plant growth system including multiple rows.

FIGS. 1A and 1B illustrate an implementation of a plant growth system 100 using multiple section 110 to provide the growth space. In illustrated configuration, each section 110 includes stacked blocks 112, and each block 112 contains one or more tubs 114. Tubs 114 are the smallest module of the growth space in plant growth system 100. In general, one or more tubs 114, e.g., four tubs 114 in FIG. 1A, may be assembled horizontally into one block 112, and multiple blocks 112, e.g., Z blocks 112 in FIG. 1A, may be stacked vertically to form a multi-layer section 110. Sections 110 may, in turn, be arranged in one or more rows. This modular hierarchy for the growth space may be constructed from factory-made modules, and the factory-made modules may reside at any of the different levels of the hierarchy. An entire section 110 including multiple blocks 112, for example, may be assembled at a factory and then shipped to a plant-growth facility as an integrated growth space module, and factory-made sections 110 may then be positioned and set up at the plant growth facility. Alternatively, each section 110 may be assembled at the plant-growth facility using blocks 112 or tubs 114 that were delivered to the facility from a manufacturer. Accordingly, blocks 112 or tubs 114 may be considered growth space modules that are building blocks of the growth space at a plant growth facility.

FIG. 1A shows a side view of a row including multiple sections 110 of the growth space of plant-growth system 100. FIG. 1A further illustrates an example implementation in which sections 110 in a row provide a multiple-layer space for growing plants. Each layer, as noted above, may include a set of tubs 114 that are at the same level or height and provide space for the roots of plants in tubs 114 with the foliage of the plants growing in open space above tubs 114. Each layer may further include plant-growth devices 116 such as lighting, ventilation fans, and plumbing that deliver light, air, and water or nutrient solution to plants in the layer.

The height of each layer may vary for different layers. More particularly, each layer may employ blocks 112 having dimensions chosen so that the vertical clearance between tubs 114 and overlying plant growth devices 116 in the blocks 112 will be sufficient for a type and growth stage of a plant to be grown in the layer.

FIG. 1B shows a top view of system 100 and illustrates how sections 110 in a growth space may be grouped or organized in multiple rows on the floor of a plant growth facility. For example, a specific section 110 may have a footprint that occupies a set amount of floor space, e.g., 1 $m^2$, and the number and arrangement of sections 110 at a facility may depend on the floor plan of the facility. Each section 110 at the facility may be assigned to a specific row number, e.g., 1 to X, and a specific section index, e.g., 1 to Y, within the assigned row. Each section 110 may thus be uniquely identified by a pair of coordinates corresponding to the row number and the section index of the section 110. The number Y of sections 110 in a particular row and the number X of rows in a plant-growth facility may be chosen according to the available floor space in the plant-growth facility. Although FIG. 1B illustrates a configuration in which rows 1 to X are straight, more generally, a row may be a curved, irregular, or any one-parameter arrangement or a sequence of sections 110.

Each section 110 in system 100 has a height, e.g., 2 m, and may include multiple layers that are distinguished by a layer index, e.g., 1 to Z. Each block 112 specifically corresponds to the growth space within a specific section 110 and a specific layer of the section 110, and each block 112 may thus be uniquely identified by a triplet of coordinates, e.g., (1,1,1) to (X,Y,Z), corresponding to row number, the section index, and the layer index. System 100 is scalable and flexible in that the number X or rows, the maximum number Y of sections 110 in a row, and the maximum number Z of layers in each section 110 may be selected or may vary as needed to efficiently accommodate or fill almost any available space in a facility. It may be noted that some rows may have fewer than the maximum number Y of sections per row and some sections 110 may have fewer than the maximum number Z of layers per section.

Each section 110, block 112, or tub 114 may have its own local control unit. For example, each section 110 may be formed (vertically) by stacking several blocks 112 together and connecting a Sectional Control Unit (SCU) 118 on top of the section 110. Vertically, each section control unit 118 may provide power to each block 112 in its section 110 and may control/monitor all devices in the section 110. Horizontally, all section control units 118 in a row and a control unit module 120 for the row may link together to form a network. Through this network, an SCU 118 may communicate with a host, e.g., a control unit 120 that runs the row of sections 110 or a master controller (not shown) that controls the entire system 100 or the entire plant growth facility.

SCUs 118 being at the top of section 110 facilitates direct connection of SCUs 118 to conventional facility infrastructure, e.g., to standard electrical outlets, provided above sections 110. The overhead power connections may simplify electrical power distribution for a vertically stacked growth space. For example, the maximum number Z of layers at a facility may depend on the height of each layer and total ceiling height of the facility. Each layer requires electrical power, and the maximum power required for each section 110 can be calculated based on the number of layers and respective distances between SCU 118 and the layers of the associated section 110. This makes the length and required gauge of all wire and cable within the same section 110 easy to calculate since cables from each SCU 118 predominantly run in the vertical direction, and an entire section 110 with layer heights specific to a plant growth facility can be built and tested during production of the section 110 at a factory. SCU 118 thus facilitates or enables factory-built cabling as opposed to requiring custom wiring at the plant growth facility. In contrast, a system employing horizontal wiring and cabling may require that the number, size, or routing of wires or cables extending through a section 110 depends on a number of sections 110 that may be strung connected together, which may be unknown when a section 110 is being built at a factory. Use of SCU 118 in each growth-space section 110 may facilitate set up of a plant growth facility because the SCUs 118 may be directly connected to conventional facility infrastructure, e.g., to standard electrical outlets, provided above the sections 110.

SDU 118 can also play a critical communication/networking role in system 100. To form a complete facility system, SCUs 118 in a row may be connected with the control unit module 120 for the row using an addressable communication link such as defined by the RS485 communication standard. With the distance between and across two adjacent SCUs 118 being known during module manufacture, a portion of the communication link may be installed in each section 110 at the factory and daisy-chained together at the plant growth facility. Alternatively, wireless network communication could be employed in a network including SCUs 118 and control unit module 120 in a row.

In addition to communications and distributing power (e.g., for lights, fans, and sensors) to each layer or block 112 in a section 110, each SCU 118 may also be the local host for its section 110 and may control and monitor all growth related activities in its section 110. For example, each SCU 118 may: control power to lights, fans, sensors, and other devices in its section 110; monitor power usage in its section 110 and generate an error message if abnormal power usage occurred; collect data through wired or wireless connections to sensors in the section 110; send sensor data to software run by control unit 120 or a facility controller (not shown); and provide location or ID information so that software can identify each block 112 at each location in the growth space and track operation and performance of blocks 112.

The implementation of FIGS. 1A and 1B has one control unit module 120 per row. Control unit module 120 may be a type of factory-made control module that differs from the growth space modules, e.g., differs from sections 110. In the implementation shown in FIG. 1A, control unit module 120 contains infrastructure 130 including a controller 122, a dosing system 124, and a liquid supply system 126 that a row of sections 110 share.

Controller 122 may include a network-linked computing system that collects and processes data from sections 110 and executes software or firmware to control plant-growth devices as needed to implement plans for growth of plants. More particularly, controller 122 may include a microcontroller on a printed circuit board connected to sensors, control relays, solenoid valves, and other control devices, for example, devices in dosing system 124 and supply system 126. Controller 122 may be programmed to handle all row-level activities such as delivering water or nutrient solution to each tub 114 in the sections 110 in a row and monitoring and controlling dosing system 124 during nutrient dosing processes. Controller 122 also communicates with all SCUs 118 connected to control unit module 120 and may operate sections 110 to work according to a growth plan. For example, controller 122 may operate dosing system 124 to mix water and nutrients specified by a growth plan and may operate liquid supply system 126 to provide, on a plan-specified schedule, the resulting nutrient solution to plants growing in the tubs 114 in that row. In particular, the controller may execute a program to operate the dosing system 124 and thereby alter the supply of the nutrients so that the nutrient solution has different ratios or concentrations of the nutrients for different plants or different plant growth stages. In one specific configuration, a manufacturer may construct individual sections 110 and control units 120 and ship the sections 110 and control units 120 to a plant growth facility, and at the plant growth facilities, multiple sections 110 may be arranged in a row and connected together and to share a control module 120.

Supply system 126 may include one or more reservoirs, one or more pumps, filters, valves and liquid return systems. Dosing system 124 may include canisters of nutrients, solenoid valves connected to controller 122 and operable to release nutrients into a reservoir in supply system 126. Dosing system 124 may further include sensors to monitor the resulting nutrient solution in the reservoir of supply system 126. Dosing system 124 may further include an antifungal or other agent such as hydrogen peroxide that control unit 120 can employ to keep water or nutrient solution free of mildew.

Figure 1C:
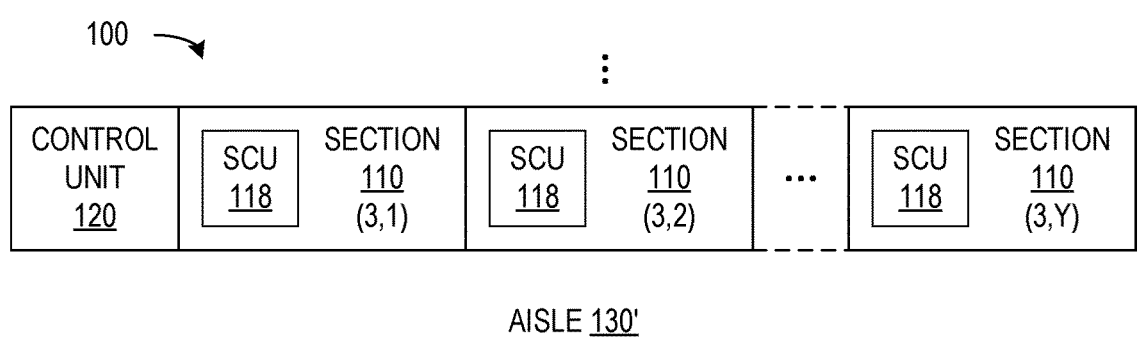
Figure 1C:
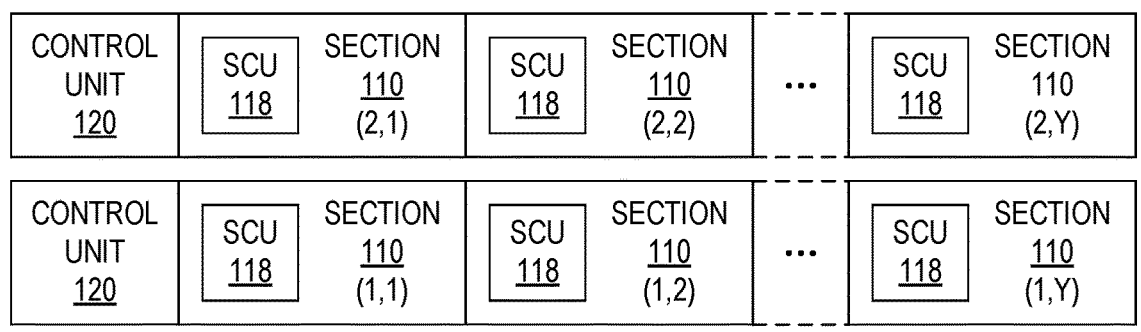

Power for sections 110 providing growth space may come down from the ceiling in a plant growth facility using power cords as described above. The power cords do not need to be particularly thick or heavy because each power cord may provide only the power needed by one section 110. Other than the power cords, all necessary wire/cable may be pre-connected in sections 110 at the factory and fixed within sections 110. Sections 110 otherwise use fluid connections to control unit module 120, so that a row of growth space may be easy to move even when system 100 is running. In particular, sections 110 and the shared control unit 120 may be physically connected, e.g., bolted, together and may have rollers or slides that facilitate movement of the row. Further, flexible power cords to sections 110 and flexible facility plumbing lines connected to control unit module 120 may provide slack so that some rows in a plant-growth facility are movable relative to other rows. This enables a file-room style, also known as roller racks on tracks, movement of an access aisle 130. FIG. 1B, for example, shows that a number X of rows of plant growth modules 110 may be arranged with space for one or more aisles 130 between adjacent rows. Each aisle 130 is an area of floor space that allows personnel or machinery to access blocks 114 of the growth space in one or both rows on either side of the aisle 130. Some configurations may include rows that do not have any adjacent aisle that permits access to that row. For example, a set of four or more rows may be arranged to provide only a single aisle 130 between two of the rows. In that case, moving a row into an aisle can fill that aisle and create a new aisle located on the opposite side of the moved row. FIG. 1B, for example, shows plant growth system 100 with aisle 130 between rows corresponding to row numbers 1 and 2, providing access to rows 1 and 2, but moving the row with row number 2 into aisle 130 reconfigures plant-growth system 100 to have no aisle between rows with row numbers 1 and 2. Instead, an aisle 130' between rows with row numbers 2 and 3 provides access to rows 2 and 3, as shown in FIG. 1C. In this way, one aisle may be sufficient for accessing any number of rows in a growth space, and floor space used for sections 110 growing plants may be maximized.

Figure 2:
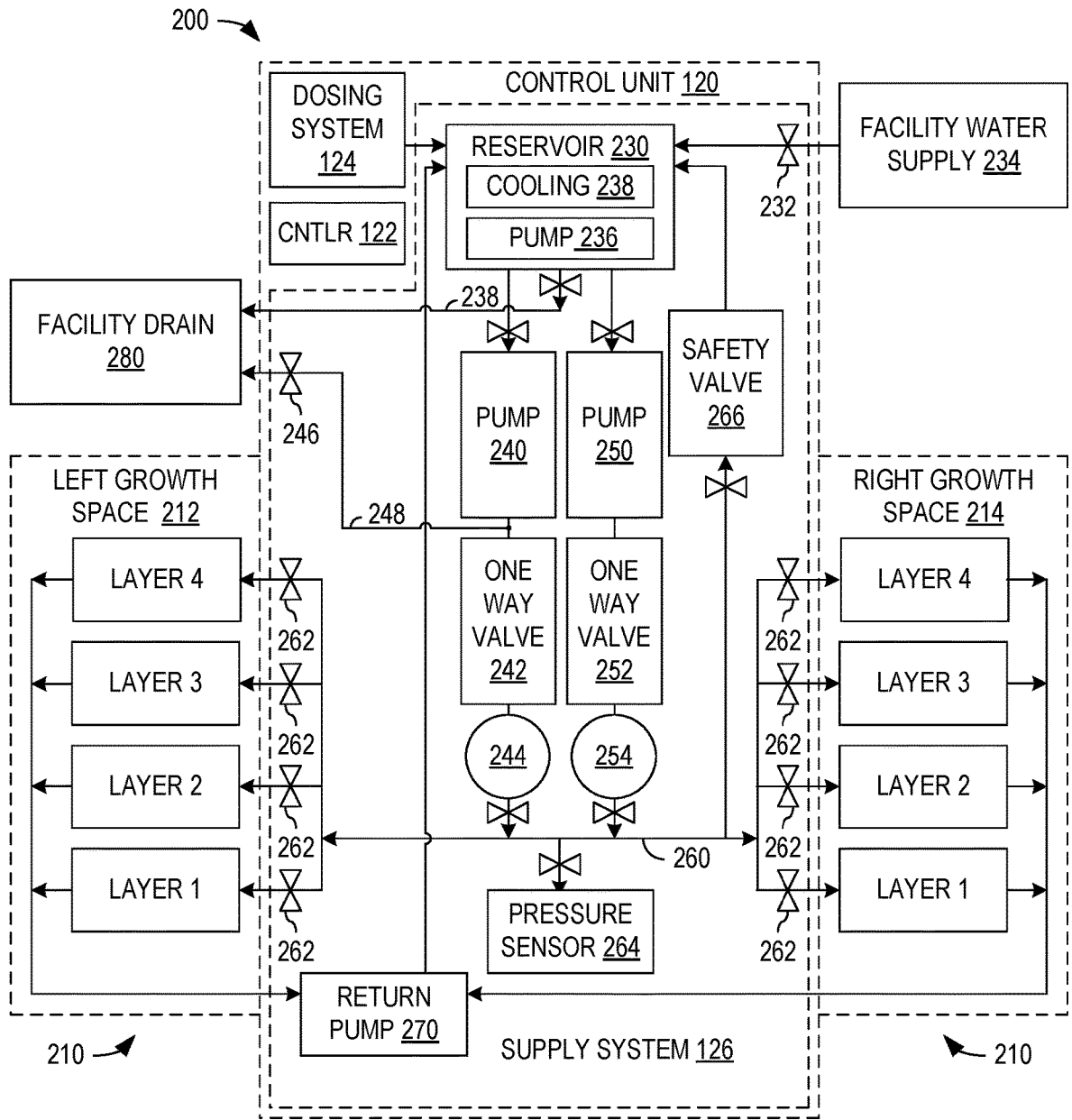
FIG. 2 is a block diagram illustrating fluid supply in a multi-layer plant growth system.

FIG. 2 is a block diagram of a row of a multi-layer plant growth system 200 and particularly illustrates details of liquid supply system 126 in an exemplary implementation of control unit module 120. In growth system 200, control unit module 120 is associated with a growth space 210 that may include multiple sections 110 as shown in FIG. 1A. Growth space 210 in the illustrated row is divided into a left growth space 212 and a right growth space 214 that may be located on opposite sides of control unit 120. This arrangement of growth space 210 may allow growth system 200 to employ smaller diameter plumbing since each plumbing line may connected to fewer, e.g., half, of the sections or other modules of growth space 210.

Supply system 126 in FIG. 2 includes a reservoir 230 that receives water through a solenoid valve 232 connected to a water supply 234 of the plant growing facility and receives plant nutrients from dosing system 124. Controller 122 controls operation of valve 232 and dosing system 124 to produce in reservoir 230 a nutrient solution having the desired chemical composition, e.g., plan-specified concentrations of nutrients in water, and a circulation pump 236 for reservoir 230 may serve to mix the nutrients in the water and may employ a filter to keep the nutrient solution clean. The minimum size of reservoir 230 generally depends on the size of growth space 210 and how frequently plants need water or nutrients from reservoir. Reservoir 230 may further include sensors (not shown). For example, controller 122 may monitor a level sensor (not shown) to ensure an adequate level of liquid in reservoir 230. A temperature sensor may be included in reservoir 230, and controller 122 can keep water temperature in reservoir 122 in a desired range, for example, by using a cooling coil (or other cooling system) 238 to cool down water in reservoir 230.

A pump 240 connected through a one-way valve 242 and a filter 244 supplies nutrient solution from reservoir 230 to a main irrigation line 260, which is connected through respective solenoid valves 262 to branch irrigation lines that may be connected to respective layers in growth space 210 or to individual blocks in the layers. To supply nutrient solution to a specific layer or block of growth space 210, controller 122 can activate pump 240 and turn on the valve 262 connected to the specific layer or block of growth space 210 while valves 262 connected to other layers or blocks are off. As a result, for the most part, one layer or one block at a time receives nutrient solution. A pressure sensor 264 and a safety valve 266 may be connected, e.g., to main irrigation line 260 or between main irrigation line 260 and reservoir 230, and may be used to sense pressure in main irrigation line 260 or to remove pressure from main irrigation line 260 in the event that sensed pressure is too high, particularly if backpressure against pump 240 is too high.

Irrigation pumps, such as pump 240, used in hydroponic or aeroponic systems usually provide water or nutrient solution to roots only when needed. This means a pump for a block of growth space may be turned on and off frequently. Frequent on-off cycling uses energy inefficiently and shortens pump life. Irrigation pump 240 may be shared by multiple layers or blocks in growth space 210 to reduce the number of times pump 240 needs to be turned on and off. Instead of shutting off pump 240 when the water needs of a block or layer are met, pump 240 may continue to run and solenoid valves 262 or similar devices may shift water flow from one layer or block to another. Pump 240, which pumps water or nutrient solution to the plants, may also be connected to drain water out from reservoir 230 when needed. For example, pump 240 may be run continuously and switched from supplying nutrient solution to layers of growth space 210 to draining liquid from reservoir 230.

In order to switch the flow from pump 240 among multiple tubs, blocks, or layers, the liquid pressure and flow of nutrient solution to the layers of growth space 210 may need to be kept within an acceptable range for supply to plants in the layers of growth space 210. One way to limit pressure adds a manual safety, diverter, or pressure relief valve 266 that diverts extra water out of main irrigation line 260, e.g., at high pressure. Such a safety valve 266 may require manual adjustment when irrigation piping condition changes. Also, a multiple-layer growth space 210 may require one safety valve for each layer because each layer has a different pressure under the same pump and needs a different setup for its safety valve. In accordance with an aspect disclosed herein, each valve 262 may be a motorized ball valve, which has a controllable aperture for fluid flow, and controller 122 may use pressure sensor 264 to measure liquid pressure and may adjust the size of the aperture of the valve 262 to maintain desired pressure or flow at the layer receiving nutrient solution. More generally, valves may be any controllable variable aperture device. (As used herein, a controllable variable aperture device is a device for controlling fluid flow that may be set to fully open an aperture for fluid flow, to close the aperture to block fluid flow, or provide one or more aperture sizes that are between open and closed sizes.)

A second nutrient solution pump 250 with one-way valve 252 and filter 254 is used in the illustrated implementation. Pump 250 connects to main irrigation line 260 and may be a redundant backup of pump 240. Alternatively, reservoir 230 may be a dual reservoir including two separate compartment for mixing of nutrient solution. With or without dual dosing systems, dual reservoirs with a dual pump and filter systems can provide continuous operation without interruption. In particular, nutrient solution may be dispensed from one compartment of reservoir 230 while another batch of nutrient solution is being mixed in another compartment of reservoir 230. Dual reservoirs may make nutrient dosing easier and more accurate.

Supply system 126 further includes a return pump 270 that may be connected to remove excess nutrient solution that might otherwise collect in the tubs in the layers of growth space 210. Return pump 270 may return the nutrient solution from growth space 210 to reservoir 230 for reuse. Alternatively, nutrient solution from reservoir 230 may be discarded through a drain line 238 or 248 respectively from reservoir 230 or pump 240 to a facility drain 280, e.g., to a sewer line or to a collection system for safe disposal of nutrient solution. The "smart" portion of control unit 120, e.g., controller 122 executing a program, may keep the liquid in reservoir 230 clean and containing the desired concentration of nutrients so that draining is minimized and the growth system may be more self-contained, only needing electricity and clean water, with efficient use and reuse of nutrients. Accordingly, liquid may be drained rarely and only when strictly necessary.

A growth tub/tray assembly may be used in growth space 210 of FIG. 2 or in the growth space of system 100 of FIG. 1A to hold plants. Such tub/tray assemblies provide operational flexibility that facilitates horticultural operations (such as germinating seeds, transplanting seedlings, and growing and harvesting plants) and service operations (such as cleaning). For example, a tub/tray assembly (or at least a tray portion of the assembly) may be sized, e.g., have a total weight and dimensions suitable for one-person operations. The assembly or tray can then be lifted, moved, and/or manipulated by a single person, which can simplify horticultural tasks and improve employee efficiency in a commercial plant growth facility. In accordance with one aspect disclosed herein, to further simplify horticultural tasks, a tub/tray assembly (or a small group of tub/tray assemblies) may be mounted as drawers that are easily shifted in or removed from a plant growth section that provides for the growth needs of one or more plants in the tub/tray assembly. In particular, a drawer may be slid so that a tray containing plants may be removed from the growth space without damaging the plants. Accordingly, some operations such as harvest and germination that do not require that much water, light, or nutrients can be performed outside a plant growth space.

Figure 3:
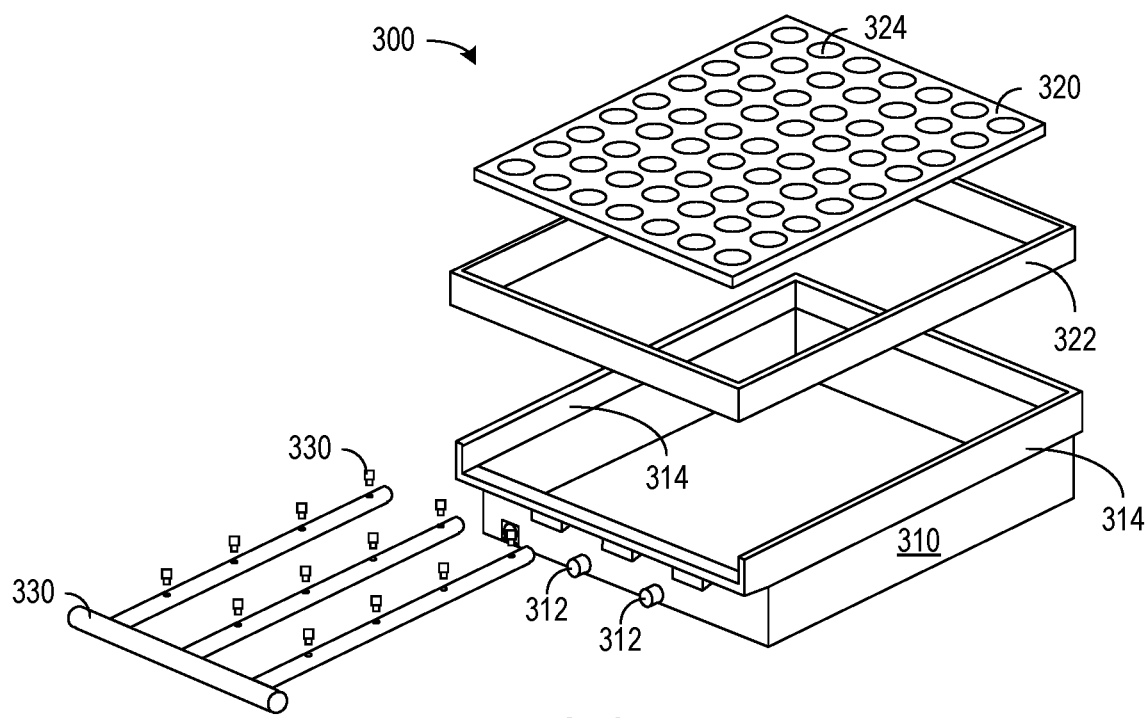
FIG. 3 shows an expanded perspective view of a tub/tray assembly used in a plant growth space.

FIG. 3 shows an exploded view of an example of a tub/tray assembly 300 that may be used in a growth space or a growth space module. Tub/tray assembly 300 includes an enclosure or tub 310 that provides space for plant roots and for containing water or a nutrient solution. For example, when tub/tray assembly 300 is in a growth space, water or nutrient solution in tub 310 may be drained out of tub 310 or otherwise kept below the level of plant roots for an aeroponic plant growth system, or water or nutrient solution in tub 310 may be kept at a level high enough to submerge plant roots for a more conventional type of hydroponic plant growth. Tub 310 may be an injection molded plastic tub having integrated inlets or outlets 312 for connection of plumbing for draining or circulating liquid held in tub 310, and a root protector (not shown) may be provided in tub 310 to prevent roots from growing into outlets 312. Each tub 310 may also include guide structures 314 around and under a mounting area for a removable tray 320. Guide structure 314 holds tray 320 and allows tray 320 to be slid forward and out of tub 310.

Tub/tray assembly 300 further includes removable plant tray 320 and a tray holder 322 that may be mounted on top of tub 310, e.g., within a mounting area defined by guide structures 314. Plant tray 320 includes an array of openings 324, which may be sized and spaced according to the desired plant density in plant tub/tray assembly 300. Each opening 324 in tray 320 may, for example, be sized to hold a small cup that holds a seed for germination, a larger cup that holds a seedling during early growth stages, or an even larger net cup that holds a growing plant until harvest. Plant tray 320 is removable from tub/tray assembly 300 and replaceable so that tub/tray assembly 300 can be fitted with a plant tray 320 suited for the growth stage of the plants to be grown in plant tub/tray assembly 300.

Tub/tray assembly 300 in the implementation of FIG. 3 further includes nutrient supply pipe or manifold 330 that supplies nutrient solution to mister nozzles 332 fitted on manifold 330. Manifold 330 with nozzles 332 may be connected to an irrigation line that supplies water or nutrient solution and may be mounted on tub 310 so that mister nozzles 332 are below tray 320 and positioned to spray nutrient solution onto the roots of plants held in tray 320. Tub/tray assembly 300 may further include a support for mounting of manifold 330 and to keep manifold 330 level.

Plant tub/tray assembly 300 may further include some electronics or other devices. For example, an image sensor, a weight sensor, or other sensors (not shown) in tub/tray assembly 300 may be used to measure or monitor growing plants. Further, a tray ID such as an embedded RFID may be integrated into plant tub/tray assembly 300, so that a tray 320 or tub 310 may be uniquely identified. Tray IDs help in tracking plants because trays may be moved to different locations, e.g., different blocks, within the growth space. In the implementation of FIG. 1A, section control unit 118 for the section 110 containing plant tub/tray assemblies 300 may collect IDs and sensor data from tub/tray assemblies 300 in the section 110 and either processes the data locally or transmits the data, e.g., to control unit 120 for further processing.

A block 112 as described with reference to FIG. 1A may contain one or more plant tub/tray assemblies 300, and blocks 112 may be a basic unit or module built at a factory and provided to a plant growth facility. In some implementations, each block 112 may include multiple tub/tray assemblies 300, a block or branch irrigation pipe, a block or branch drainage pipe, lighting, an air movement device (e.g., fans or air ducts), and other devices that assist plant growth, and such blocks 112 may be vertically stacked as described above with reference to FIG. 1A.

Figure 4:
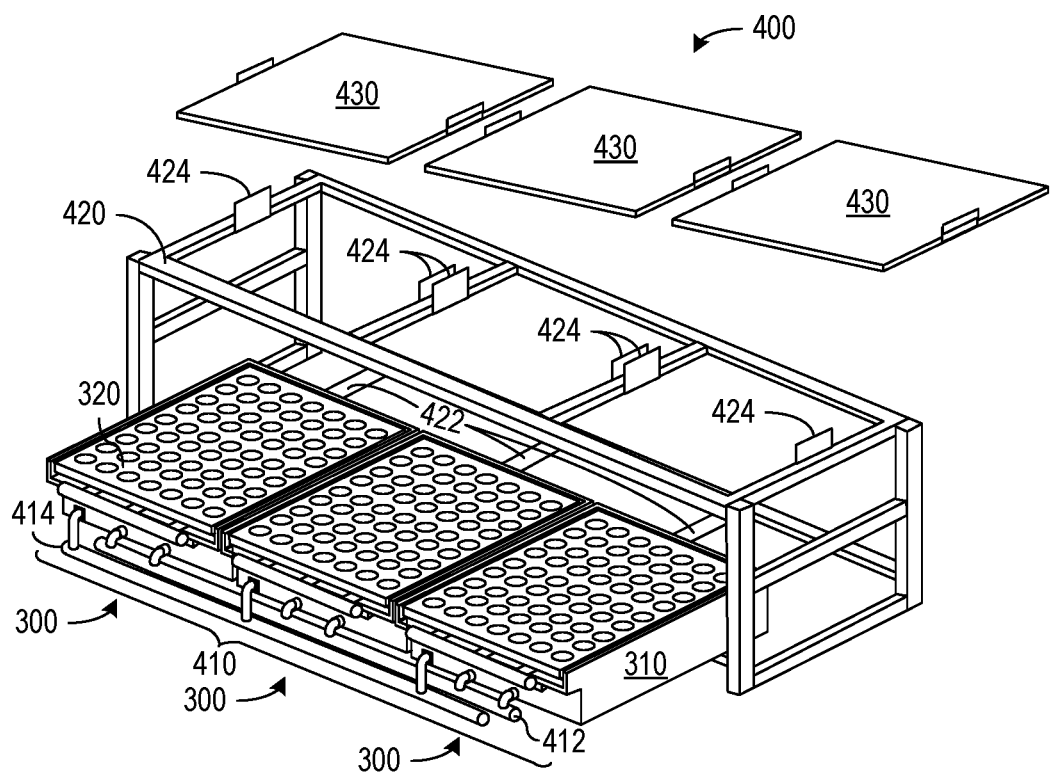
FIG. 4 shows an expanded perspective view of a block of a plant growth space including multiple tub/tray systems that form a drawer for growing plants.

Blocks 112 in a section 110 may employ a drawer system for tub/tray assemblies 300. FIG. 4, for example, illustrates a growth space block 400 that may form a layer of a section 110. Growth space block 400 includes one or more tub/tray assemblies 300 that may be connected together as part of a unit 410 that fits in an enclosure 420. Unit 410 may include multiple tub/tray assemblies 300, a drain pipe 412 connected to outlets 312 on tubs 310, and a pressurized (input) pipe 414 for water or nutrient solution that may be supplied to manifolds 330 within the tub/tray assemblies 300 forming unit 410. Rubber connectors or other flexible or releasable plumbing or fittings (not shown) may connect drain 412 to a row or the facility's plumbing and may connect pressurized pipe 414 to a source of water or nutrient solution, e.g., to liquid supply system 126 for the row. See FIG. 1A or 2.

Enclosure 420 includes a structure or frame that may be mounted on or may form a part of the structure of a section, and enclosure 420 may occupy an area that is about the same as the floor space area of the section. A height of enclosure 420 may be adjustable or selected according to the desired height of the layer, e.g., according to the anticipated height of plants to be grown in block 400. Enclosure 420 may further include mounting and height adjustment structures 424 for installation of over-plant devices 430. Over-plant devices 430 may include, for example, lighting and ventilation devices, that provide the needs of plants growing in block 400.

Enclosure 420 may further include guides 422 that are under or at the sides (not shown) of tub/tray assemblies 300 to facilitate sliding unit 410 partly or fully out of enclosure 420, for example, for planting of plants in unit 410, for rearranging plants to provide room for further growth, or for harvest. In one implementation, unit 410 may be slid far enough that enclosure 420 does not interfere with removal of trays 320 from tubs 310 while trays 320 contain plants. Alternatively, tub/tray assemblies 300 may be entirely removed from enclosure 420. Unit 410 may thus operate as a drawer mounted to slide relative to enclosure 420. Alternatively, unit 410 may be fixed in enclosure 420, and trays 320 may operate as drawers that slide relative to tubs 310.

Harvest often takes considerable time and labor at the site where plants grow. During harvest, growers often cannot plant or grow new plants in a portion of a growth space being harvested before all mature plants are harvested from that portion. After harvest, growers may need to take time to plant seeds in place of the harvested plants. A drawer style tray such as described above with reference to FIGS. 3 and 4 with valves (manual or electronic valves) on pressurized pipe and drain pipe allows each layer or unit 410 to be serviced individually while other layers are still operated normally. The drawer system also allows growers to take entire tray 320 of plants out of a growth space and immediately place a new tray 320 of younger plants in that layer of growth space, while other layers still continue to operate normally. This may maximize the utilization of plant growth systems that provide water, nutrient dosing, $CO_2$ enrichment, and lights needed for plant growth. Further, harvesting and packaging of plants in the removed tray may be completed at a different location from the plant growth facility, so that harvesting may also be more efficient, for example, because a removed drawer-style tray may be fed into an automatic harvest/cleaning/packing machine for post growth processing.

Systems disclosed herein may support both submerged-root hydroponics and aeroponics and may switch from one to the other based on the situations encountered during plant growth or based on the actual plants being grown. In particular, a valve that blocks (or permits) water in a tub/tray from returning to a reservoir may close (or open) to switch a block from aeroponic to submerged-root hydroponic operation (and vice versa). In one configuration, a system automatically may switch from aeroponic operation to submerged-root hydroponic operation during a power outage (or to save power) while keeping plants alive.

Although particular implementations have been disclosed, these implementations are only examples and should not be taken as limitations. Various adaptations and combinations of features of the implementations disclosed are within the scope of the following claims.

What is claimed is:

1. An aeroponic plant-growth system comprising:
    a growth space including a plurality of layers respectively at a plurality of heights, each layer comprising one or more plant holders and one or more misters, each of the misters being positioned to apply mist to roots of a plant in at least one of the plant holders; and
    a control unit comprising:
    a liquid supply system coupled to the misters in the layers, the liquid supply system comprising:
    a pump; and
    a plurality of valves coupled to the pump and respectively to the layers; and
    a controller configured to execute a program that continuously operates the pump while operating the valves to control a plurality of liquid flows to the misters in the respective layers, the operation of the valves regulating the liquid flows according to the heights of the respective layers.

2. The system of claim 1, wherein the growth space further comprises:
    an enclosure; and
    the plant holders comprise a plurality of tub/tray assemblies stacked vertically in the enclosure, each of the tub/tray being in a different one of the layers of the growth space.

3. The system of claim 2, wherein each of the tub/tray assemblies includes a tub and a tray mounted in the tub.

4. The system of claim 3, wherein the trays are mounted to slide out of the respective tubs for removal while the trays hold plants.

5. The system of claim 1, further comprising irrigation plumbing extending from the liquid supply system to the misters, the irrigation plumbing permitting removal of any of the drawers while the irrigation plumbing continues service to others of the drawers.

6. The system of claim 1, wherein the controller operates the pump to keep the pump continuously on while the controller turns on the liquid flow to one of the layers and turns off the liquid flow to another of the layers.

7. The system of claim 1, wherein the valves have adjustable aperture sizes.

8. The system of claim 7, wherein the controller operates a selected one of the valves to provide the liquid flow to the layer coupled to the selected valve and shut off the liquid flows through others of the valves, the controller selecting the adjustable aperture size of the selected valve based on the height of the layer connected to the selected valve to provide the liquid flow from the selected valve with a pressure acceptable for the misters to supply mist to plants.

9. The system of claim 8, further comprising a pressure sensor coupled to sense liquid pressure in the liquid supply system, wherein the controller operates the selected one of the valves to have the adjustable aperture size be selected additionally based on a pressure sensed by the pressure sensor.

10. The system of claim 7, wherein each of the valves comprises a motorized ball valve.

11. The system of claim 1, wherein:

the control unit comprises a factory-made control module; and the growth space comprises a plurality of factory-made sections that are connected together and connected to the factory-made control unit at a plant growth facility.

12. The system of claim 1, wherein the control unit further comprises:

a reservoir; and a dosing system coupled to supply water and nutrients to the reservoir, the controller controlling operation of the dosing system to create a nutrient solution in the reservoir, wherein:

the liquid supply system supplies the nutrient solution from the reservoir in the liquid flows to the misters in the plurality of layers.

13. The system of claim 12, wherein the controller executes the program to operate the dosing system and thereby alter the supply of the nutrients so that the nutrient solution has different ratios of the nutrients for different plants or different plant growth stages.

14. The system of claim 12, wherein the controller executes the program to operate the dosing system to dispense an agent that keeps the nutrient solution clean.

15. The system of claim 1, wherein the controller operates the valves to turn the liquid flows on and off and when any of the valves provides liquid flow to the misters, the controller operates the valve to maintain a desired pressure of the liquid flow at the misters regardless of the height of the layer containing the misters.

16. The system of claim 1, wherein the controller further operates the valves to maintain a desired pressure of the liquid flow at the misters regardless of the height of the layer containing the misters.

17. An aeroponic plant-growth system comprising:

a growth space including a plurality of layers respectively at a plurality of heights, each layer comprising one or more plant holders and one or more misters, each of the misters being positioned to apply mist to roots of a plant in at least one of the plant holders; and a control unit including a liquid supply system coupled to the misters in the layers, the liquid supply system comprising:

a pump providing a liquid flow;

a plurality of valves coupled to the pump and respectively to the layers; and a controller configured to execute a program that continuously operates the pump while operating the valves to turn on one or more of the valves and thereby start the liquid flow to one of the layers when turning off one or more of the valves and thereby stop the liquid flow to another of the layers.

* * * * *